United States Patent [19]

Wallach

[11] Patent Number: 4,855,090
[45] Date of Patent: Aug. 8, 1989

[54] METHOD OF PRODUCING HIGH AQUEOUS VOLUME MULTILAMELLAR VESICLES

[75] Inventor: Donald F. H. Wallach, Brookline, Mass.

[73] Assignee: Micro-Pak, Inc., Wilmington, Del.

[21] Appl. No.: 78,658

[22] Filed: Jul. 28, 1987

Related U.S. Application Data

[63] Continuation-in-part of Ser. No. 25,525, Mar. 13, 1987, abandoned.

[51] Int. Cl.[4] .................. A61K 9/66; A61K 37/22; B01J 13/02
[52] U.S. Cl. .................................... 264/4.1; 264/4.3; 424/1.1; 424/85.2; 424/85.4; 424/89; 424/101; 424/450; 428/402.2; 436/829; 514/885
[58] Field of Search ................. 264/4.1, 4.3; 428/402.2; 424/450; 436/829

[56] References Cited

U.S. PATENT DOCUMENTS

| | | | |
|---|---|---|---|
| 3,957,971 | 5/1976 | Oleniacz | 424/70 |
| 4,133,874 | 1/1979 | Miller et al. | 428/402.2 X |
| 4,217,344 | 8/1980 | Vanlerberghe et al. | 424/60 |
| 4,235,871 | 11/1980 | Papahadjopoulos et al. | 424/450 |
| 4,241,046 | 12/1980 | Papahadjopoulous et al. | 424/450 X |
| 4,247,411 | 1/1981 | Vanlerberghe et al. | 264/4.6 |
| 4,348,329 | 9/1982 | Chapman | 260/403 |
| 4,356,167 | 10/1982 | Kelly | 424/450 |
| 4,377,567 | 3/1983 | Geho | 424/1.1 |
| 4,485,054 | 11/1984 | Mezei et al. | 264/4.6 |
| 4,536,324 | 8/1985 | Fujiwara et al. | 252/311 |
| 4,551,288 | 11/1985 | Kelly | 264/4.6 |
| 4,564,599 | 1/1986 | Janoff et al. | 436/507 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,692,433 | 9/1987 | Hostetler et al. | 514/12 |
| 4,695,554 | 9/1987 | O'Connell et al. | 436/528 |
| 4,772,471 | 9/1988 | Vanlerberghe et al. | 424/450 |

FOREIGN PATENT DOCUMENTS

| | | |
|---|---|---|
| 0032578 | 7/1984 | European Pat. Off. . |
| 3410602 | 9/1984 | Fed. Rep. of Germany . |
| 59-106423 | 6/1985 | Japan . |
| 61-207324 | 9/1986 | Japan . |
| 1539625 | 1/1979 | United Kingdom . |
| 2078543 | 1/1982 | United Kingdom . |
| 2079179 | 1/1982 | United Kingdom . |
| 2147263 | 5/1985 | United Kingdom . |
| 8501440 | 4/1985 | World Int. Prop. O. . |

OTHER PUBLICATIONS

"Liposomes," Edited by Marc J. Ostro, The Liposome Co., Princeton, N.J., Marcel Dekker, Inc., New York, pp. 246–249, (1983).
Gregoriadis (1976) New Eng. J. Med. (1976) 295:704–711.
Szoka, Francis and Papahadjopoulos, Demetrios. Procedure for preparation of liposomes with large internal aqueous space and high capture by reverse-phase evaporation. Proc. Natl. Acad. Sci. U.S.A. (1978) 75:4194–4198.
Puisieux and Poly, "Problems Technologiques Poses Par L'Utilisation Des Liposomes Comme Vecteurs De Substances Medicamenteuses, Encapsulation, Sterilisation, Conservation." in *Les Liposomes*. Puisieux and Delattre, Eds. Techniques et Documentation La Voisier, Paris, (1980) pp. 73–113.
Dousset and Douste-Blazy, "Methodes de Preparation des Liposomes." in *Les Liposomes*. Puisieux and Delattre, Eds. Techniques et Documentation La Voisier Paris, (1980) pp. 41–70.
Handjani-Vila, Ribier, and Vanlerberghe, "Les Niosomes," in *Les Liposomes*. Puisieux and Delattre, Eds. Techniques et Documentation La Voisier Paris, (1980) pp. 297–313.
Philippot et al., A very mild method allowing the encapsulation of very high amounts of macromolecules into very large (1000nm) unilamellar liposomes. Biochem. Biophys. Acta (1983) 734:137–143.
Ribier and Hanjani-Vila, Bilayer fluidity of non-ionic vesicles. An investigation by differential polarized phase fluorometry. Colloids and Surfaces (1984) 10:155–161.
Philippot et al., Extemporaneous preparation of large unilamellar liposomes. Biochem. Biophys. Acta (1985) 821:79–84.
Baillie et al., The preparation and properties of niosomes-non-ionic surfactant vesicles, J. Pharm. Pharmacol, (1985) 37:863–868.
Baillie et al., Non-ionic surfactant vesicles, niosomes, as a delivery system for the anti-leishmanial drug, sodium stibogluconate. J. Pharm. Pharmacol. (1986) 38:502–505.

*Primary Examiner*—Richard D. Lovering
*Attorney, Agent, or Firm*—Lahive & Cockfield

[57] ABSTRACT

Disclosed is a new method of producing high aqueous volume multilamellar lipid vesicles. The method uses less expensive materials than those commonly used, is faster than classical methods, and produces vesicles with a much higher encapsulated mass and captured volume than was previously available.

34 Claims, No Drawings

METHOD OF PRODUCING HIGH AQUEOUS VOLUME MULTILAMELLAR VESICLES

REFERENCE TO RELATED APPLICATION

This application is a continuation-in-part of U.S. Patent Application Ser. No. 025,525, filed Mar. 13, 1987 and now abandoned.

BACKGROUND OF THE INVENTION

Liposomes or lipid vesicles have been known since at least 1965. There are three general types of liposomes: multilamellar vesicles (MLV), onion-like structures having a series of substantially spherical shells formed of lipid bilayers interspersed with aqueous layers, ranging in diameter from about 0.1–4 $\mu$m; large (greater than 1 $\mu$m diameter) unilamellar vesicles (LUV) which have a lipid bilayer surrounding a large, unstructured aqueous phase; and small unilamellar vesicles (SUV) which are similar in structure to the LUV's except their diameters are less than 0.2 $\mu$m. Because of the relatively large amount of lipid in the lipid bilayers of the MLV's, MLV's are considered best for encapsulation or transportation of lipophilic materials whereas the LUV's, because of their large aqueous/lipid volume ratio, are considered best for encapsulation of hydrophilic molecules, particularly macromolecules. SUV's have the advantage of small size, which allows relatively easy access to the cells of tissue, but their small volume limits delivery of hydrophilic aqueous materials to trace amounts. However, SUV's may be useful in the transportatio of lipophilic materials.

All of the early liposome studies used phospholipids as the lipid source for the bilayers. The reason for this choice was that phospholipids are the principal structural components of natural membranes. However, there are many problems using phospholipids for liposome-type structures. First, isolated phospholipids are subject to degradation by a large variety of enzymes. Second, the most easily available phospholipids are those from natural sources, e.g., egg yolk lecithin, which contain polyunsaturted acyl chains that are subject to autocatalyzed peroxidation. When peroxidation occurs, the liposome structure breaks down, causing premature release of encapsulated materials and the formation of toxic peroxidation byproducts. This problem can be avoided by hydrogenation but hydrogenation is an expensive process, thereby raising the cost of the starting materials. Cost is a third problem associated with the use of phospholipids on a large scale. A kilogram of egg yolk lecithin pure enough for liposome production, presently costs in excess of $40,000. This is much to high a cost for a starting material for most applications.

Because of the high cost and additional problems in using phospholipids, a number of groups have attempted to use synthetic amphiphiles in making lipid vesicles. For example, Vanlerberghe and others working for L'Oreal have used a series of synthetic polymers, primarily polyglycerol derivatives, as alternatives to the phospholipids. Similarly, Kelly and a group at Sandoz, Inc. have tried aliphatic lipids.

Recently, there has been some indication, particularly from the L'Oreal group, that commercially available surfactants might be used to form the lipid bilayer in liposome-like multilamellar lipid vesicles. Both surfactants and phospholipids are amphiphiles, having at least one lipophilic acyl or alkyl group attached to a hydrophilic head group. The hydrophilic head groups in the surfactants which have been tried include polyoxyethylene or polyglycerol derivatives. The head groups are attached to one or more lipophilic chains by ester or ether linkages. Commercially available surfactants include the BRIJ family of polyoxyethylene acyl ethers, the SPAN sorbitan alkyl esters, and the TWEEN polyoxyethylene sorbitan fatty acid esters, all avauilable from ICI Americas, Inc. of Wilmington, Del.

No matter what starting material is used to form the MLV's, substantially all of the methods of vesicle production reported in the literature use either the original Bangham method, as described in Bangham et al., J. Mol. Biol., 13:238–252 (1965), or some variation thereof. The basic approach followed starts with dissolving the lipids, together with any other lipophilic substances including cholesterol, in an organic solvent. The organic solvent is removed by evaporation using heat or by passing a stream of an inert gas (e.g., nitrogen) over the dissolved lipid to remove the solvent. The residue is then slowly hydrated with an aqueous phase, generally containing electrolytes and any hydrophilic biologically active materials, to form large multilamellar lipid membrane structures. In some variations, different types of particulate matter or structures have used during the evapoartion to assist in the formation of the lipid residue. The basis for these experiments are that by changing physical structure of the lipid residue, better vesicles may form upon hydration. Two recent review publications, Szoka and Papahdjopoulos, ann. Rev. Biophys. Bioeng. 9:467–508 (1980), and Dousset and Douste-Blazy (in *Les Liposomes*, Puisieux and Delattre, Editors, Tecniques et Documentation Lavoisier, Paris, pp.41–73 (1985)), summarize the methods which have been used tomake MLV's.

Once the MLV's are made, it is necessary to determine the effectiveness of the process. Two measurements commonly used to determine the effectiveness of encapsulation of biological materials in liposomes or lipid vesicles are the mass of substance encapsulated per unit mass of the lipid ("encapsulated mass") and captured volume.

The captured volume is the amount of solvent trapped within the vesicles. The captured volume is defined as the concentration of the aqueous fraction inside the vesicle divided by the concentration of lipid in the vesicle, normally given in ml/gm lipid.

Multilamellar lipid vesicles made using the classic methods have a low encapsulated mass for hydrophilic materials, normally in the order of 5–15%. In addition, the captured volume of solvent is normally in the order of 2–4 ml/g lipid. However, the encapsulated mass for lipophilic materials is much better in the multilamellar liposomes. Therefore, multilamellar liposomes made using the classical procedures are considered good for encapsulating lipophilic (hydrophobic) material but not hydrophilic.

The small unilamellar liposomes, which range is diameter from 20–50 nm, have a very low captured volume (approximately 0.5 ml/g) and also a very low encapsulated mass for hydrophilic materials (0.5–1%). However, since the lipid bilayer constitutes 50–87% of the total volume, these SUV's are excellent at transporting small quantities of lipohilic material. They also can be used to transport very small quantities of hydrophilic material to tissues where the MLV's or LUV's cannot reach.

Because of the problems in encapsulating large volumes and obtaining high encapsulated mass for hydrophilic materials, LUV's have been investigated. LUV's have large captured volumes (approximately 35 ml/gm lipid) and high encapsulated mass for hydrophilic materials (40–50%) but they are very poor in encapsulating hydrophibic or lipophilic materials. Because of these characteristics, LUV's are best suited to encapsulation of hydrophilic materials, including macromolecules. However, there are problems with the use of LUV's. Since there is only a single lipid bilayer surrounding a large aqueous center, the LUV's tend to be less stable then the other liposomes and more easily subject to degradation. Further, the low lipid/aqueous volume ratio makes it difficult to use LUV's for transport of any lipophilic materials.

Although there have been some experiments reported in the literature on using synthetic surfactants rather than phospholipids as a source for making multilamellar lipid vesicles, there are no reports showing any improvement in the ability to encapsulate either small or large hydrophilic molecules using these materials. In addition, there is no report of increased stability for lipid vesicles made with these materials. Therefore, the literature has given no indication that liposomes manufactured with these synthetic materials will be useful to achieve the hydrophilic and macromolecule delivery objects sought in the liposome field.

A further problem associated with multilamellar lipid vesicles (including the small unilamellar vesicles which are normally manufactured by sonication of the multilamellar vesicles) manufactured using standard methods is that these current processes are both slow and relatively inefficient in terms of material. For example, the standard time to manufacture multilamellar lipid vesicles is in the order 2–20 hours. If SUV's are required, the sonication which breaks the multilamellar lipid structures into SUV's takes additional time. This slow processing is unwieldy and expensive for any large scale use of lipid vesicles.

Accordingly, it is an object of the invention to provide a rapid and efficient process for the formation of multilamellar vesicles.

It is a further object of the invention to develop multilamellar vesicles with high encapsulated mass for hydrophilic materials and high captured volume.

It is another object of the invention to form lipid membrane structures without the use of organic solvents or detergents.

It is still a further object of the invention to provide a method for the rapid, efficient encapsulation of biologically active macromolecules into vesicles made of relatively inexpensive, readily available surfactants.

These and other objects and features of the invention will be apparent from the detailed description and the claims.

SUMMARY OF THE INVENTION

The present invention provides a method of preparing multilamellar lipid vesicles which is rapid, efficient and produces vesicles which have high encapsulated mass for hydrophilic material and high captured volumes. The invention also provides a method of encapsulating lipophilic or hydrophilic materials in high aqueous volume multilamellar vesicles with high efficiency.

In order to prepare the vesicles, a lipophilic phase is formed by blending a surfactant with a sterol and a charge producing amphiphile while maintaining the temperature of the phase above the melting point of the surfactant. The lipophilic phase is then combined with an excess of an aqueous phase under high-shear conditions and elevated temperature in order to form the multilamellar vesicles. Whereas the temperature need not be kept constant for all the formation steps, in all cases the temperature must be above the melting point of the surfactant.

surfactants useful in the process for forming these vesicles include polyoxyethylene fatty ethers, preferably having the structure

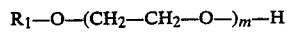

where $R_1$ is $CH_3$-$(CH_2)_n$, n ranges from 11 to 15, and m is 2 to 4. Although other polyoxyethylene ethers can be used, the most preferred materials are polyoxyethylene (2) cetyl ether and polyoxyethylene (4) lauryl ether.

An alternative group of lipids which are also useful in the invention, are the polyglycerol fatty ethers, preferably having the structure

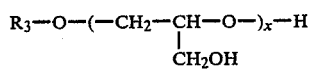

where $R_3$ is $CH_3$-$(CH_2)_y$, y ranges from 11 to 15, and x ranges from 1 to 3.

The purpose of the sterol in the vesicles is to buffer the thermotropic phase transition of the membrane layer with insures optimal size and provides high stability, including stability near the transition temperature of the lipid. The most preferred sterol is cholesterol but any sterol having similar properties will provide similar results.

Vesicles made without charge producing materials lack the capacity for high volume uptake and efficient incorporation of hydrophilic molecular and macromolecules; they also have the tendency to aggregate or clump, making them unusable for most applications. Because of this, a charge producing material is used in the method of the invention to provide a net charge, either positive or negative, to the formed vesicle. The preferred negative charge producing materials are selected from a group consisting of dicetyl phosphate, cetyl sulphate, certain long chain fatty acids, retinoic acid, phosphatidic acid, phosphatidyl serine, and mixtures thereof.

In order to provide a net positive charge to the vesicles, long chain amines, long chain pyridinium compounds (e.g., cetyl pyridinium chloride), quaternary ammonium compounds or mixtures thereof can be used. A preferred material for causing a positive charge is hexadecyl trimethylammonium bromide, a potent disinfectant. The use of this disinfectant as a positive charge producing material within the vesicles provides a secondary advantage as the vesicles deteriorate; they act as a sustained release germicide carriers.

The vesicles may also include targeting molecules, either hydrophilic or amphiphilic, which can be used to direct the vesicles to particular targets in order to allow release of the material encapsulated in the vesicle at a specified biological location. If hydrophilic targeting molecules are used, they can be coupled directly or via a spacer to an OH residue of the polyoxyethylene or polyglycerol portion of the surfactant, or they can be coupled, using state of the art procedures, to molecules such as palmitic acid or phosphatidylethanolamine. If spacers are used, the targeting molecules can be interdigitating with the hydrophilic core of the bilayer membrane. Preferred hydrophilic targeting molecules include monoclonal antibodies, lectins, and peptide hormones.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Preferred amphiphilic targeting molecules are neutral glycolipids, galactocerebrosides, (e.g., for hepatic galactosyl receptors), or charged glycolipids, such as gangliosides.

Vesicles made using the methods of the present invention can be used in diagnostic testing, e.g., agglutination testing of immunological systems. The vesicles can also be used as markers or labels for visualization, e.g., for radiography.

In another aspect, the invention provides a method of encapsulating hydrophilic or lipophilic materials. In order to encapsualte lipophilic materials within the vesicle, the lipophilic materials are blended into the lipophilic base formed of the surfactant, a sterol and a charge producing material at a temperature above the melting temperature of the surfactant. The formation of the vesicle is otherwise carried out as previously described.

In order to encapsulate a hydrophilic material, the lipophilic phase is made as previously described and the hydrophilic material to be encapsulated is added to the aqueous phase. Hydrophilic materials which can be encapsulated include macromolecules, viruses, immunological adjuvants such as muramyl dipeptide, peptide hormones such as insulin, glucagon, and pituitary hormones, growth factors such as angiogenic, epithelial and epidermal growth factors, lymphokines such as interleukin-2 and interferon, blood proteins such as hemoglobin, water-soluble plant hormones and pesticides, radionucleotides, and contrast dyes for radiological diagnosis. Examples of lipophilic materials which can be encapsulated include steroid hormones, organic pesticides, fungicides, insect repellants, and lipophilic vitamins and derivatives. A more complete listing of the types of materials that could be used in lipid vesicles is included in an article by Gregoriadis, New Engl. J. Med. 295:704–711 (1976).

The following description and examples more fully illustrate the invention.

DESCRIPTION

The present invention features a process of making a new type of multilamellar lipid vesicle with large aqueous volume using surfactants as the lipid source in a rigid production method, a method of encapsulating hydrophilic or lipophilic materials within this type of multilamellar lipid vesicle, and the high aqueous volume multilamellar lipid vesicles themselves. Based on encapsulated mass and captured volume, the multilamellar lipid vesicles of the invention appear better suited to the encapsulation and delivery of hydrophilic materials, including macromolecules, than multilamellar lipid vesicles known in the art. Further, by using the most preferred materials to form the multilamellar lipid vesicles, these vesicles appear to tolerate a broader range of pH than classic liposomes or other known multilamellar lipid vesicles and are not as susceptible to attack by oxidative systems, e.g., peroxidases and superoxide-generating systems of phagocytes. The multilamellar lipid vesicles are also much cheaper to make because of a lower cost of the starting materials.

In broad terms, the multilamellar lipid vesicles of the present invention are made by raising the temperature of the lipid structural materials, which may be polyoxyethylene fatty ethers or polyglycerol fatty ethers, to a temperature above their melting point so that they are liquid. A sterol, preferably cholesterol, together with a charge producing material and any lipophilic materials to be encapsulated is blended into the liquid surfactant to form a lipophilic phase. This lipophilic phase is then forced into an excess of an aqueous phase, also at a temperature above the melting point of the surfactant, using a high shear device. If any hydrophilic materials are to be encapsulated within the multilamellar lipid vesicles, they are included in the aqueous phase. Since the polyoxyethylene fatty ethers useful in the invention have low melting points, bioactive hydrophilic materials which are temperature-sensitive can still be encapsulated without damage. This permits the present method to be used for a broad range of materials.

Anionic or cationic amphiphiles are incorporated into the surfactant to yield a net negative or positive charge. The incorporation of a charge-bearing material into the lipid structure stabilizes the lipid structure and provides rapid dispersion. If such a charge is not used, any vesicles formed will aggregate unless they are kept at very low concentrations. The charged material is also required for a large aqueous volume to be encapsulated. The amount of charged amphiphile does not have to be large, 0.5 moles percent—5 moles percent (based on the concentration of the surfactant) is sufficient to provide proper charge to the vesicles.

Cholesterol, or another sterol with similar chemical properties, is incorporated into the lipid structure of the multilamellar vesicles in order to provide better stability and buffer the thermotropic phase transition of the membrane layer, e.g., providing stability of the membrane structure at temperature near the transition temperature of the lipid. The cholesterol also permits optimum size of the finished vesicle. The preferred surfactant/cholesterol molar ratio ranges from about 3–20, and depends to some extent on whether cholesterol competes with any lipophilic material to be encapsulated.

Although the polyoxyethylene and polyglycerol surfactants described herein are the best presently known for carrying out the method of the invention, it is possible that phospholipids or other surfactants could be used to form vesicles by this method. However, many of these phospholipids and other surfactants have such high melting temperature that it would be impractical to use these for encapsulating biologically active materials which are temperature sensitive. Further, if more unsaturated lipids are used, they are more susceptible to oxidative breakdown.

Once the lipophilic phase is formed, it is necessary to hydrate it using a high shear technique. There are a large variety of devices available on the market which can provide this high shear. Devices which could be used include a microfluidizer such as is made by Biotechnology Development Corporation, a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the multilamellar lipid vesicles of the present invention.

Once the multilamellar lipid vesicles are formed, the size can be changed or the structure modified by sonication or mechanical shear. Devices for carrying this out, as well as the general procedures, are known to those skilled in the art and are commonly used in the liposome field.

If the multilamellar lipid vesicles of the present invention are used as a drug-delivery system, there is no particular limitation on how they can be used. For example, the vesicles may be dispersed directly in suspension, in aerosol form, topically, or in a gel. If used for agglutination testing or some other type of marker use, lipophilic dyes which are taken up directly into the lipid layers may be used.

In addition to use as a drug or macromolecule delivery system, the multilamellar lipid vesicles of the invention have substantial other uses. For example, the vesicles can be used as an adjuvant in order to improve the immunological response of injected material. In addition, the high aqueous volume allows the use of the multilamellar lipid vesicles of the invention as moisturizers or skin creams with advantageous results. The high captured volume/lipid ratio is such that more moisture is provided to the skin using the vesicles of the invention than is available from conventional skin care creams.

The invention will be more apparent from the following, non-limiting Examples.

EXAMPLE 1

The multilamellar lipid vesicles of this Example were made using one of the most preferred materials, polyoxyethylene (2) cetyl ether. Although syringes were used as described to provide the high shear in this and the following Examples, any high shear device could have been used.

TABLE 1

| | |
|---|---|
| Polyoxyethylene (2) cetyl ether | 0.696 gm |
| Cholesterol | 0.073 gm |
| Dicetyl phosphate | 0.055 gm |
| 5 mM phosphate, 150 mM NaCl, pH 7.4 | 10.0 ml |

Table 1 lists the materials and proportions used in preparing the multilamellar lipid vesicles for this Example. The polyoxyethylene (2) cetyl ether, cholesterol and dicetyl phosphate were placed in a 5 ml syringe and heated to 40° C., a temperature abovde the melting point of the lipid. The dicetyl phosphate provided a net negative charge to the final membrane structure. The lipophilic phase which resulted after the heating and blending of the lipophilic components was forcibly injected, via a three-way stopcock, into an aqueous phase consisting of 10 ml of 5 mM phosphate buffer containing 150 mM NaCl, pH 7.4. The phosphate buffer, which was contained in a 25 ml syringe, was also at 40° C. The process of injection of the lipophilic phase into the aqueous phase took less than five seconds. The resulting mixture was then forced into a second 25 ml syringe at a linear flow rate of 8-12 x $10^2$ cm/sec through an orifice about 1 mm in diameter. The mixture was driven continously back and forth between the two 25 ml syringes for approximately 2 minutes, providing the liquid shear necessary to make the high volume lipid vesicles. A milky suspension containing the multilamellar lipid vesicles resulted. The multilamellar lipid vesicles were separated by centrifugation at 10,000 rpm for 15 minutes in a Beckman Instrumental co. J-21 centrifuge, forming a low density phase on top of the aqueous solution.

The multilamellar lipid vesicles formed would not pass through a 0.8 μm filter. Upon sonication for 6 minutes in a Branson sonicator, the lipid membrane structures attained the size of normal multilamellar vesicles, passing through a 0.45 μm filter. Upon sonification for an additional 6 minutes, the structures were reduced enough in size to pass through a 0.2 μm filter.

EXAMPLE 2

In this Example, the identical procedure was used as in Example 1 except the dicetyl phosphate, which provided a negative charge in Example 1, was replaced by cetyl trimethylammonium. The exact proportions used in this Example are shown in Table 2.

TABLE 2

| | |
|---|---|
| Polyoxyethylene (2) cetyl ether | 0.696 gm |
| Cholesterol | 0.073 gm |
| Cetyl trimethylammonium | 0.036 gm |
| 5 mM phosphate, 150 mM NaCl, pH 7.4 | 10.0 ml |

The positively charged multilamellar vesicles produced again could not pass through a 0.8 μm filter but upon sonification for 6 minutes, they passed freely through a 0.45 μm filter. Upon further sonification for an additional 6 minutes, the lipid membrane structures again passed freely through a 0.2 μm filter.

EXAMPLE 3

In this Example, a larger scale test was made using the same materials as Example 1. Three grams of lipid were employed. The molar proportions of the material used, as well as the volume of aqueous phase, are disclosed in Table 3.

TABLE 3

| | |
|---|---|
| Polyoxyethylene (2) cetyl ether | 33 mM |
| Cholesterol | 11 mM |
| Dicetyl phosphate | 1.5 mM |
| 5 mM phosphate, 150 mM NaCl, pH 7.4 | 50 ml |

The polyoxyethylene (2) cetyl ether, the cholesterol, and the dicetyl phosphate, a total of 3 gm of lipid, were placed in a 25 ml syringe and heated to 40° C. The mixture was then forcibly injected, via a three-way stopcock, into 50 ml of the phosphate buffer, also at 40° C., contained in a 60 ml syringe. This process took less than 10 seconds. The resulting mixtures were then forced into a second 60 ml syringe at a flow rate of 8-12 x $10^2$ cm/sec through an orifice about 1 mm in diameter. The resulting mixture was driven continuously back and forth between the two 60 ml syringes for about two minutes, yielding a cream. Upon centrifugation at 10,000 rpm for 15 minutes, the lipid membrane structure was separated as a layer atop the nonincorporated aqueous phase. The captured aqueous volume in different experiments was 7-20.8 ml/g lipid, an amount much greater then the 2-4 ml/g lipid generally observed for multilamellar lipid membrane structures. A 1/100 dilution of the vesicles was found to be stable against aggreagation for thirty days at ambient temperature.

EXAMPLE 4

In this Example, substantially the same methods were used as in Example 3 except polyoxyethylene (4) lauryl ether was used in place of the polyoxyethylene (2) cetyl ether. Since the lauryl ether is a liquid at ambient temperature, no heating was required. Three grams of total lipid was used, with the proportions given in Table 4.

TABLE 4

| | |
|---|---|
| Polyoxyethylene (4) lauryl ether | 33 mM |
| Cholesterol | 11 mM |
| Dicetyl phosphate | 1.5 mM |
| 5 mM phosphate, 150 mM NaCl, pH 7.4 | 50 ml |

After formation of the multilamellar lipid vesicles and separation by centrifugation, the captured volume was measured and found to be 8 ml/g lipid. This is entirely surprising since the multilamellar lipid vesicles formed in this experiment passed freely through a 0.2 μm filter without sonification. Because of this small size, the lauryl vesicles may have similar access to organs that SUV's have while still allowing high captured volume and encapsulation efficiency.

EXAMPLE 5

In this Example, a macromolecule, specifically hemoglobin, was used to show encapsulation efficiency for the multilamellar lipid vesicles of the invention. The polyoxyethylene (2) cetyl ether was used to prepare the lipid membrane structures. Table 5 lists the concentrations.

TABLE 5

| | |
|---|---|
| Polyoxyethylene (2) cetyl ether | 3.1 gm |
| Cholesterol | 0.7 gm |
| Dicetyl phosphate | 0.13 gm |
| Red cell hemolysate (10 mg Hb/ml) | 50 ml |

The red cell hemolysate was formed by lysing fresh, washed human erythrocytes in hypotonic phosphate buffer to give a hemoglobin concentration of 10 mg/ml. This lipid, cholesterol and dicetyl phosphate were placed in a 10 ml syringe and heated to 40° C. The mixture was then forcibly ejected, via a three-way stopcock, into 50 ml of the red cell hemolysate contained in a 60 ml syringe. This injection took less than 5 seconds. The resulting mixture was then forced into a second 60 ml syringe at a flow rate of $8-12 \times 10^2$ cm/sec through an orifice of about 1 mm. The resulting mixture was driven continuously back and forth between the two syringes for approximately 2 minutes, yielding a dark pink cream.

Sevel ml of the resulting cream was mixed with 3 ml of a Ficoll-Paque density barrier (Pharmacia) and centrifugegd at 10,000 rpm for 15 minutes. Any unincorporated hemoglobin stays in the Ficoll-Paque density barrier whereas hemoglobin associated with the lipid vesicles will float with the lipophilic phase to the top of the aqueous phase. The lipophilic, vesicle-containing phase was pink colored and separated from the top of the density barrier. One ml aliquots of the two fractions (the lipid phase and the density barrier phas) were dissolved in 4 ml of soluene (0.5n quaternary ammonium hydroxide in toluene, made by Packard) and the hemoglobin content was determined by measuring the absorbance of the Soret band (420 nm). The Ficoll-Paque had a 0.42 O.D. while the lipid membrane structures had a 1.46 O.D., showing that about 22 mg of hemoglobin per gram liquid was associated with the lipid membrane structures. The corresponding aqueous volume uptake was approximately 8 ml/g.

Gassing with moist nitrogen caused the characteristic spectral change in the hemoglobin associated with the lipid membrane structures, showing a transformation from oxyhemoglobin to deoxyhemoglobin. After reexposure to ambient oxygen, the spectral change occurred, showing a transformation back to oxyhemoglobin. This illustrates that the hemoglobin is unharmed by the encapsulation process.

The hemoglobin containing structures were kept in buffer for 11 days at 40° C. then repurified on a Ficoll-Paque density barrier. Seventy percent of the hemoglobin that was encapsulated was still found to be present in the lipid phase. the hemoglobin-containing lipid membrane structures still illustrated the deosygenation-reoxygenation reaction. A similar experiment at 17 days showed that 62% of the hemoglobin initially incorporated was still retained and still exhibited normal deoxygenation-reoxygenation.

A similar experiment was fun using 30 mg hemoglobin/ml, a three-fold increase in concentration. An expected increase in hemoglobin encapsulation, 58 mg/g lipid, was observed.

EXAMPLE 6

In this Example, polyoxyethylene (10) cetyl ether was compared with polyoxyethylene (2) cetyl ether in order to determine encapsulated mass and captured volume. The proportions of the materials used were identical to those shown in Table 1. Table 6 gives the results of this experiment.

TABLE 6

| Surfactant | Volume taken up (ml/g lipid) | Hemoglobin taken up mg/g lipid |
|---|---|---|
| Polyoxyethylene (2) cetyl ether | 7-9 | 20-60 |
| Polyoxyethylene (10) cetyl ether | 2-3 | <3 |

For the polyoxyethylene (2) cetyl ether, 7–9 ml solvent/g lipid was taken up into the aqueous volume and the encapsulated mass for the hemoglobin was 20–60 mg/g lipid. In contrast, using the polyoxyethylene (10) cetyl ether only 2–3 ml solvent/g lipid was taken up and the encapsulated mass was less then 3 mg/g lipid. The values for the polyoxyethylene (10) cetyl ether are substantially the same as those shown in the literature using classic encapsulation methods, and phospholipids, using phospholipids and classic encapsulation methods for the formation of MLV. This shows that the method of the invention works for a variety of materials; however, the polyoxyethylene (2) cetyl ether yields a clear advantage.

EXAMPLE 7

In this Example, a lipophilic molecule, specifically retinoic acid, used to demonstrate the capacity of the multilamellar vesicles of this invention to encapsulate lipophilic molecules. The polyoxyethylene (2) cetyl ether was used as the lipid structural material of the vesicles. The retinoic acid is incorporated into the lipophilic phase of the lipid membrane structures. Two and a half grams total lipid was employed in the proportions given in Table 7 and the method used was that of Example 3.

TABLE 7

| | |
|---|---|
| Polyoxyethylene (2) cetyl ether | 33 mM |
| Cholesterol | 6 mM |
| Dicetyl phosphate | 1.5 mM |
| Retinoic Acid | 0.67 mM |
| 5 mM phosphate, 150 mM NaCl, pH 7.4 | 40 ml |

In accordance with the method of this invention, the polyoxyethylene (2) cetyl ether, cholesterol, dicetyl phosphate and retinoic acid were blended at 40° C. in a 10 ml syringe and the mixture was then forcibly injected into 40 ml 5mM phosphate, 150 mM NaCl, pH 7.4, likewise at 40° C., in a 60 mol syringe. The mixture was then subjected to high fluid shear by two minutes of mixing through a 1 mm orifice into another 60 ml syringe, yielding a yellow cream.

Upon centrifugation at 15,000 rpm for 15 minutes, the lipid vesicles separated as a yellow layer atop the nonincorporated aqueous phase. The isolated lipid vesicles could be diluted without further volume uptake to form a stable, homogeneous suspension. The measured incorporation of aqueous phase into the lipid membrane structures was 18 ml/g. This very high value under the conditions employed may be due to the added net negative charge contributed by the retinoic acid. The encapsulation of retinoic acid was 8 mg/g lipid (>99%).

EXAMPLE 8

In this Example, retinoic acid was used to replace dicetyl phosphate in providing the negative charge for lipid vesicles prepared with polyoxyethylene (2) cetyl and cholesterol. Two and a half grams of a lipid mixture with the molar proportions in Table 8 was employed. The method used was identical with that of Example 3.

TABLE 8

| | |
|---|---|
| Polyoxyethylene (2) cetyl ether | 33 mM |
| Cholesterol | 6 mM |
| Retinoic acid | 1.5 mM |
| 5 mM phosphate, 150 mM NaCl, pH 7.4 | 40 ml |

After formation of the multilamellar vesicles and separation by centrifugation, the aqueous volume taken up was measured and found to be 12 ml/g lipid. The retinoic acid encapsulated was 17.5 mg/g/

EXAMPLE 9

This Example demonstrates the capacity of the lipid vesicles formed by the method of this invention from polyoxyethylene (2) cetyl ether were to incorproate a different lipophilic material, the insect repellent N,N-diethyl meta-toluamide. Two and a half gram of lipid was used in the proportions given in Table 9. The method used was the same as Example 7 with the N,N-diethyl meta-toluamide replacing the retinoic acid.

| | |
|---|---|
| Polyoxyethylene (2) cetyl ether | 33 mM |
| N,N—diethyl meta-toluamide | 11 mM |
| Cholesterol | 5 mM |
| Dicetyl phosphate | 1.5 mM |
| 5 mM phosphate, 150 mM NaCl, pH 7.4 | 40 ml |

Upon centrifugation at 15,000 rpm for 15 minutes, the lipid membrane structures separated as a white layer atop the nonincorporated aqueous phase. This could readily be redispersed and diluted into a uniform suspension without separation of a low-density phase of N,N-diethyl meta-toluamide. The volume uptake was 10 ml/g lipid and >99% of the N,N-diethyl meta-toluamide was retained by the lipid membrane vesicle. Separate experiments showed that if cholesterol is eliminated from the system, the liposomes quickly lost the N,N-diethyl meta-toluamide.

EXAMPLE 10

This Example demonstrates the capacity of the lipid vesicles formed by the method of this invention to encapsulate supramacromolecular structures, specifically avian encephalitis (AE) virus, a 17 nm virion. The proportions and method used are identical to those of Example 5 except the red blood lysate was replaced by a solution of the AE virus. The results are shown in Table 10.

TABLE 10

| SERUM DILUTION | 1:00 | 1:2 | 1:4 | 1:8 | 1:16 | 1:32 |
|---|---|---|---|---|---|---|
| SAMPLE | | | | | | |
| AE VIRUS | 1.47 | 0.75 | 0.48 | 0.24 | 0.21 | 0.17 |
| standard | | | | | | |
| anD used for | | | | | | |
| incorporation | | | | | | |
| AQUEOUS RESIDUE | 0.08 | 0.08 | 0.10 | 0.08 | 0.12 | 0.99 |
| CONTROL AVERAGE = 0.077 | | | | | | |
| STANDARD-CONTROL | 1.39 | 0.67 | 0.40 | 0.16 | 0.13 | 0.09 |
| RESIDUE-CONTROL | 0.00 | 0.00 | 0.02 | 0.00 | 0.04 | 0.02 |

As is evident from the results of Table 10, at least 75% of AE is taken up into the multilamellar vesicles of this invention, indicating their potential usefulness in the transportation of viruses and plasmids.

EXAMPLE 11

In this Example, the percent uptake of an aqueous based solution was determined for multilamellar vesicles of the invention. The vesicles were made as disclosed in Example 1 except 2.5 grams of lipid was used to form the lipophilic phase while different amounts of a 0.25 N sorbitol solution was offered as an aqueous phase. The lipid was then separated by density gradient centrifugation and the volumes were measured. Table 11 illustrates the captured volume in ml/g of lipid.

TABLE 11

| Offered volume | Volume taken up | Volume taken up/g | % uptake |
|---|---|---|---|
| 10 ml | 10 ml | 4 | 100 |
| 20 ml | 20 ml | 8 | 100 |
| 30 ml | 30 ml | 12 | 100 |
| 40 ml | 40 ml | 16 | 100 |
| 50 ml | 48 ml | 19.2 | 96 |
| 60 ml | 52 ml | 20.8 | 87 |

As is evident from the results shown in Table 11, the multilamellar vesicles of the present invention have much greater captured volume than conventional multilamellar vesicles.

What is claimed is:

1. A method of preparing high aqueous volume multilamellar lipid vesicles consisting essentially of the steps of:
   A. Providing a solventless non-aqueous liphpilic phase by blending a polyoxyethylene fatty ether surfactant with a sterol and a charge producing amphiphile while maintaining the temperature of said lipophilic phase above the melting point of said surfactant;

B. Providing an aqueous phase formed of an aqueous solvent and any aqueous soluble materials to be encapsulated; and
C. Combining said non-aqueous lipophilic phase with a substantial excess of said aqueous phase in a single step under shear conditions while maintaining the temperature of the mixture above the melting point of said surfactant;
whereby said high aqueous volume multilamellar lipid vesicles are formed in less than two minutes without forming a separable hydrated lamellar phase.

2. The method of claim 1 wherein said surfactant comprises a polyoxyethylene fatty ether having the structure $$R_1-O-(CH_2-CH_2CH_2-O-)_m-H$$

where $R_1$ is $CH_3-(CH_2)_n$, n ranges from 11 to 15, and m is 2 to 4.

3. The method of claim 2 wherein said sterol comprises cholesterol or a derivative thereof.

4. The method of claim 3 wherein said charge producing amphiphile is a negative charge producing material selected from a group consisting of dicetyl phosphate, cetyl sulphate, long chain fatty acids, retinoic acid, phosphatidic acid, phosphatidyl serine, and mixtures thereof.

5. The method of claim 3 wherein said charge producing amphiphile is a positive producing material selected from a group consisting of long chain amines, long chain pyridinium compounds, quaternary ammonium compounds, and mixtures thereof.

6. The method of claim 3 further comprising coupling a hydrophilic targeting molecule selected from a group consisting of monoclonal antibodies, lectins and peptide hormones to said surfactant, said hydrophilic targeting molecule being coupled directly to an OH residue of the polyoxyethylene portion of said surfactant.

7. The method of claim 3 further comprising coupling a hydrophilic targeting molecule selected from a group consisting of monoclonal antibodies, lectins and peptide hormones to said surfactant, said hydrophilic targeting molecule being coupled through a spacer molecule to an OH residue of the polyoxethylene portion of said surfactant.

8. The method of claim 3 further comprising coupling a hydrophilic targeting molecule selected from a group consisting of monoclonal antibodies, lectins and peptide hormones to said surfactant, said hydrophilic targeting molecule being coupled directly to an acyl chain interdigitating with said surfactant.

9. The method of claim 3 further comprising coupling a hydrophilic targeting molecule selected from a group consisting of monoclonal antibodies, lectins and peptide hormones to said surfactant, said hydrophilic targeting molecule being coupled through a spacer molecule to an acyl chain interdigitating with said surfactant.

10. The method of claim 3 wherein said polyoxyethylene fatty ether comprises polyoxyethylene (2) cetyl ether.

11. The method of claim 3 wherein said polyoxyethylene fatty ether comprises polyoxyethylene (4) lauryl ether.

12. The method of claim 3 wherein said charge producing molecule comprises retinoic acid.

13. A method for encapsulating an amphiphilic material within a multilamellar lipid vesicle consisting essentially of the steps of:

A. Providing a solventless non-aqueous lipophilic phase by blending a polyoxyethylene fatty ether surfactant with a sterol and a charge producing amphiphile while maintaining the temperature of said lipophilic phase above the melting point of said surfactant, and blending said amphiphilic material to be encapsulated into said lipophilic phase;
B. Providing an aqueous phase formed of an aqueous solvent and any aqueous soluble materials to be encapsulated; and
C. Combining said non-aqueous lipophilic phase with a substantial excess of said aqueous phase in a single step under shear conditions while maintaining the temperature of the mixture above the melting point of said surfactant;
whereby said multilamellar lipid vesicles are formed and said amphiphilic material is encapsulated in less than two minutes without forming a separable hydrated lamellar phase.

14. The method of claim 13 wherein said surfactant comprises a polyoxyethylene fatty ether having the structure $$R_1-O-(CH_2-CH_2-O-)_m-H$$

where $R_1$ is $CH_3-(CH_2)_n$, n ranges from 11 to 15, and m is 2 to 4.

15. The method of claim 14 wherein said sterol comprises cholesterol or a derivative thereof.

16. The method of claim 15 wherein said charge producing amphiphile is a negative charge producing material selected from a group consisting of dicetyl phosphate, cetyl sulphate, long chain fatty acids, retinoic acid, phosphatidic acid, phosphatidyl serine, and mixtures thereof.

17. The method of claim 15 wherein said charge producing amphiphile is a positive charge producing material selected from a group consisting of long chain amines, long chain pyridinium compounds, quaternary ammonium compounds, and mixtures thereof.

18. The method of claim 15 wherein said polyoxyethylene fatty ether comprises polyoxyethylene (2) cetyl ether.

19. The method of claim 15 wherein said polyoxyethylene fatty ether comprises polyoxyethylene (4) lauryl ether.

20. A method of encapsulating hydrophilic material within a high aqueous volume multilamellar lipid vesicle consisting essentially of the steps of:

A. Providing a solventless non-aqueous lipophilic phase by blending a polyoxyethylene fatty ether surfactant with a sterol and a charge producing amphiphile while maintaining the temperature of said lipophilic phase above the melting point of said surfactant;
B. Providing an aqueous phase by blending said hydrophilic material to be encapsulated in an aqueous solvent; and
C. Combining said non-aqueous lipophilic phase with a substantial excess of said aqueous phase in a single step under shear conditions while maintaining the temperature of the mixture above the melting point of said surfactant;
whereby said high aqueous volume multilamellar lipid vesicles are formed and said hydrophilic material is encapsulated in less than two minutes without forming a separable hydrated lamellar phase.

21. The method of claim 20 wherein said surfactant comprises a polyoxyethylene fatty ether having the structure $$R_1-O-(CH_2-CH_2-O-)_m-H$$

where $R_1$ is $CH_3-(CH_2)_n$, n ranges from 11 to 15, and m is 2 to 4.

22. The method of claim 21 wherein said sterol comprises cholesterol or a derivative thereof.

23. The method of claim 22 wherein said charge producing amphiphile is a negative charge producing material selected from a group consisting of dicetyl phosphate, cetyl sulphate, long chain fatty acids, retinoic acid, phosphatidic acid, phosphatidyl serine, and mixtures thereof.

24. The method of claim 22 wherein said charge producing amphiphile is a positive charge producing material selected from a group consisting of long chain amines, long chain pyridinium compounds, quaternary ammonium compounds, and mixtures thereof.

25. The method of claim 22 wherein said polyoxyethylene fatty ether comprises polyoxyethylene (2) cetyl ether.

26. The method of claim 22 wherein said polyoxyethylene fatty ether comprises polyoxyethylene (4) lauryl ether.

27. The method of claim 20 wherein said hydrophilic material comprises a macromolecule.

28. The method of claim 27 wherein said hydrophilic material comprises hemoglobin.

29. The method of claim 20 wherein said hydrophilic material comprises a peptide hormone.

30. The method of claim 20 wherein said hydrophilic material comprises a growth factor.

31. The method of claim 20 wherein said hydrophilic material comprises a lymphokine.

32. The method of claim 20 wherein said hydrophilic material comprises interleukin.

33. The method of claim 20 wherein said hydrophilic material comprises interferon.

34. The method of claim 20 wherein said hydrophilic material comprises a virus.

* * * * *